United States Patent [19]

De Ruiter

[11] Patent Number: Plant 6,237

[45] Date of Patent: Aug. 2, 1988

[54] MINIATURE ROSE PLANT NAMED 'RUIFIFTY'

[75] Inventor: Gijsbert De Ruiter, Hazerswoude, Netherlands

[73] Assignee: De Ruiter's Nieuwe Rozen B.V., Hazerswoude, Netherlands

[21] Appl. No.: 887,705

[22] Filed: Jul. 21, 1986

[51] Int. Cl.[4] ..... A01H 5/00

[52] U.S. Cl. ..... Plt./10

[58] Field of Search ..... Plt./9-10

*Primary Examiner*—Robert E. Bagwill

*Attorney, Agent, or Firm*—Charles W. Rummler

[57] ABSTRACT

A new variety of miniature rose characterized by a continuous and profuse production of very large Poppy Red blooms carried on very long, strong stems; the blooms are approximately 1¼ inches in diameter; its formed flowers having large petals which tend to marginally turn under and form points; and its free branching and vigorous growth habit produces a dwarf, compact, busy, free blooming plant suitable for use as a pot plant as well as for a garden decoration.

1 Drawing Sheet

BACKGROUND OF THE NEW PLANT

My new variety of rose plant is the result of breeding efforts carried on by me at Hazerswoude, Holland, with the object of producing miniature rose plants suitable for production of flowering pot plants as well as to be useful for garden decoration. This plant originated as a seedling derived by my crossing of an unnamed seedling with the variety 'Ruimin' (unpatented). The form and beauty of the flowers of this new plant and its very fine growth habit led me to propagate this plant, by cuttings, through several successive generations, which showed that the novel characteristics of this plant would hold true from generation to generation. Commercial propagation of this plant, by budding, is now being carried on in Holland.

DESCRIPTION OF THE DRAWING

My new variety of rose plant is illustrated by the accompanying photographic drawing, showing the vegetative growth and flowers of this variety and as depicted, the color is as true as is reasonably possible to make the same in a color illustration of this character. The specimens illustrated were grown with three plants in one pot in a greenhouse at Hazerswoude, Holland.

DESCRIPTION OF THE NEW PLANT

The following combination of advantageous characteristics is observed in the new variety:

(a) Readily propagated and grown on its own roots by cuttings;

(b) Exhibits a well balanced, compact and vigorous growth habit which is extremely floriferous;

(c) Blooms carried in clusters as well as one per stem;

(d) Exhibits an excellent aptitude for greenhouse forcing as a flowering pot plant and also as a very good comportment when used as an outdoor garden plant;

(e) Bloom color in general is Poppy Red.

The following is a detailed description of my new rose plant, the observations being made from plants grown in a greenhouse in Hazerswoude, Holland, in early December.

Throughout this specification color designations are based upon The R.H.S. Colour Chart published by The Royal Horticultural Society of London, England.

THE PLANT

Origin: Sport.

Parentage:

*Seed parent.*—An unnamed and unpatented rose plant.

*Pollen parent.*—'Ruimin' (unpatented).

Classification:

*Botanic.*—Rose Hybrid.

*Commercial.*—Miniature Rose.

Form: Bush.

Growth habit: Vigorous and upright with little to moderate branching.

Height: About 18–22 cm.

Growth rate: Fast.

Canes:

*Length.*—8–10 cm. (measured from base of the stem to the flower cluster).

*Diameter.*—1.8–2.4 mm.

*Color.*—Green, 137C.

Foliage:

*Quantity.*—Normal.

*Number of leaves.*—8–11.

*Shape of leaf.*—Odd pinnate.

*Color.*—New foliage — Yellow-Green, 147A. Old foliage — Green, 137A.

*Size.*—Length — About 45–50 mm. Width — About 40–45 mm.

*Leaflets.*—Number: 3 to 5. Shape: Elliptic. Texture: Firm. Margins: Serrated. Color: Dark Red. Shape base of terminal leaflet: Obtuse. Petioles: Color: Green under side with prickles on vein. Stipules: Small, slightly bearded.

Thorns:

*Quantity.*—On main canes from base, few. On laterals from main canes, few.

*Form.*—Flat, thin, relatively long.

*Color when young.*—Light Green.

THE BUD

Form: Round ovate.

Size:

*Diameter.*—8 to 9 mm.

*Depth.*—11 to 13 mm.

Color:

*When sepals first divide.*—Red, 40D.

*When half blown.*—Upper side of petals, Orange Red, 42D. Lower side of petals, Red, 44D.

Sepals:

*Color.*—Yellow-Green, 146A; extensions absent in two, medium in three.

Receptacle:

*Color.*—Yellow-Green, 146B.

*Shape.*—Pitcher shaped.

*Size.*—Small. Length — 3/16 inch. Width — 3/16 inch.

*Surface.*—Smooth, dull.

*Peduncle.*—Length: 18-25 mm. Color: Yellow-Green, 144A.

THE FLOWER

Blooming habit: Continuous and abundant.

Borne: Single and in clusters of two to five.

Size:

*Average open size.*—1¼" to 1½".

Form:

*Upper part.*—Flat.

*Under part.*—Flat.

Stem:

*Length.*—Medium.

Petalage:

*Number of petals.*—70 to 80.

*Shape.*—Elliptic.

*Texture.*—Medium, thick, firm.

*Arrangement.*—Generally inbricated; petaloids in center.

*Color.*—Upper side of petals: Marginal zone — Red, 40D. Middle zone — Red, 40D. Basal zone — Yellow, 10E. Basal spot — Green-Yellow, 1B. Reverse side: Marginal zone — Orange Red, 33C. Middle zone — Orange Red, 33C. Basal zone — Yellow, 10B. Basal spot — Green-Yellow, 1B.

Variegations: Occasional white midrib.

Discoloration: After seven days, color becomes Red, 49A.

Fragrance: None.

Persistence: The petals hand on and dry.

Lasting quality: On the plant, long lasting.

REPRODUCTIVE ORGANS

Stamens:

*Number.*—20-25.

*Arrangement.*—Regular around the styles.

*Anthers.*—Size: Small-short. Color: Yellow-Orange, 23A.

*Filaments.*—Length: About 1-2 mm. Color: Yellow-Orange, 16C.

*Pollen.*—Color: Yellow-Orange, 22A.

Pistils:

*Number.*—30-35.

*Styles.*—Length: 4-5 mm. Color: Yellow-Green, 145C.

*Stigmas.*—Color: Red, 37B.

Ovaries: Normal.

I claim:

1. A new and distinct variety of rose plant of the miniature class, substantially as herein shown and described, characterized by being a dwarf, compact, free blooming plant, having blooms of Poppy Red color, approximately 1¼ inch in diameter, with petals of heavy substance, and being suitable for use as a pot plant as well as for garden decoration.

* * * * *

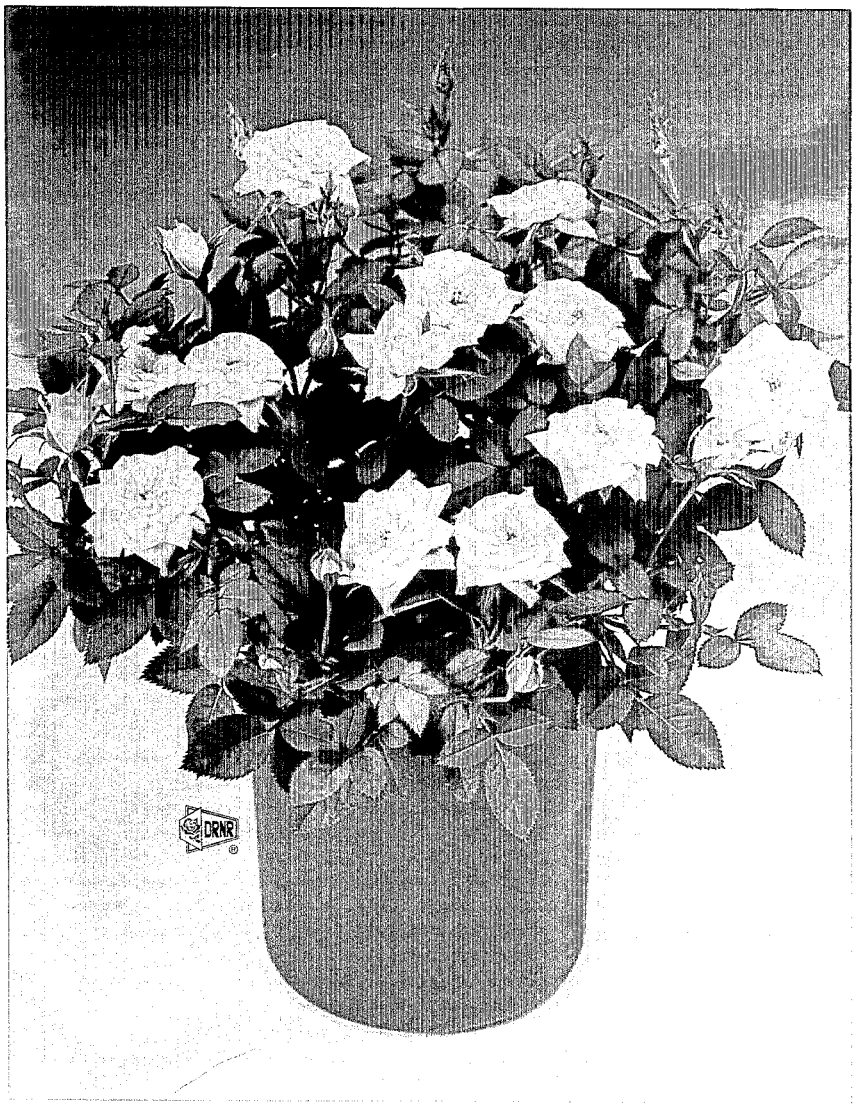
DRNR